United States Patent [19]

Loeppert

[11] Patent Number: 4,760,250
[45] Date of Patent: Jul. 26, 1988

[54] OPTOELECTRONICS SYSTEM FOR MEASURING ENVIRONMENTAL PROPERTIES HAVING PLURAL FEEDBACK DETECTORS

[75] Inventor: Peter V. Loeppert, Hoffman Estates, Ill.

[73] Assignee: Spectramed, Inc., Newport Beach, Calif.

[21] Appl. No.: 912,286

[22] Filed: Sep. 29, 1986

[51] Int. Cl.⁴ .............................. H01J 5/16; G01J 1/32
[52] U.S. Cl. .................................... 250/227; 250/205; 250/231 R
[58] Field of Search ........... 250/345, 344, 339, 231 R, 250/227, 226, 205, 462.1; 356/441, 442, 41, 39

[56]  References Cited
U.S. PATENT DOCUMENTS

| | | | |
|---|---|---|---|
| 3,799,672 | 3/1974 | Vurek | 356/41 |
| 4,200,110 | 4/1980 | Peterson et al. | 356/39 |
| 4,476,870 | 10/1984 | Peterson et al. | 356/41 |
| 4,514,860 | 4/1985 | Adolfsson et al. | 250/227 |
| 4,523,279 | 6/1985 | Sperinde et al. | 356/41 |
| 4,529,875 | 7/1985 | Brogardh et al. | 250/231 R |
| 4,531,230 | 7/1985 | Brogardh | 250/227 |
| 4,543,961 | 10/1985 | Brown | 250/231 R |
| 4,587,101 | 5/1986 | Marsoner et al. | 250/462.1 |

Primary Examiner—David C. Nelms
Assistant Examiner—William L. Oen
Attorney, Agent, or Firm—Lyon & Lyon

[57] ABSTRACT

An optoelectronic system for measuring at least one property of an environment includes a first light source for generating light at a first wavelength, first feedback means coupled to the first light source for maintaining the light from the first light source at a substantially constant level, a second light source for generating light at a second wavelength, second feedback means coupled to the second light source for maintaining the light from the second light source at a substantially constant level, a sensor to be placed in an environment, the sensor being responsive to a change in a property of an environment, the sensor generating first and second optical output signals representing a change in the light from the first and second light sources, respectively, due to a property of the environment, an optical waveguide for transmitting light from the first and second light sources to the sensor, a detector for detecting the first and second optical output signals, an optical waveguide for transmitting the first and second optical output signals from the sensor to the detector and apparatus coupled to the detector for determining the value of the property of the environment from the first and second optical output signals.

14 Claims, 5 Drawing Sheets

OPTICAL CONNECTIONS

PO₂ OPTICAL SYSTEM

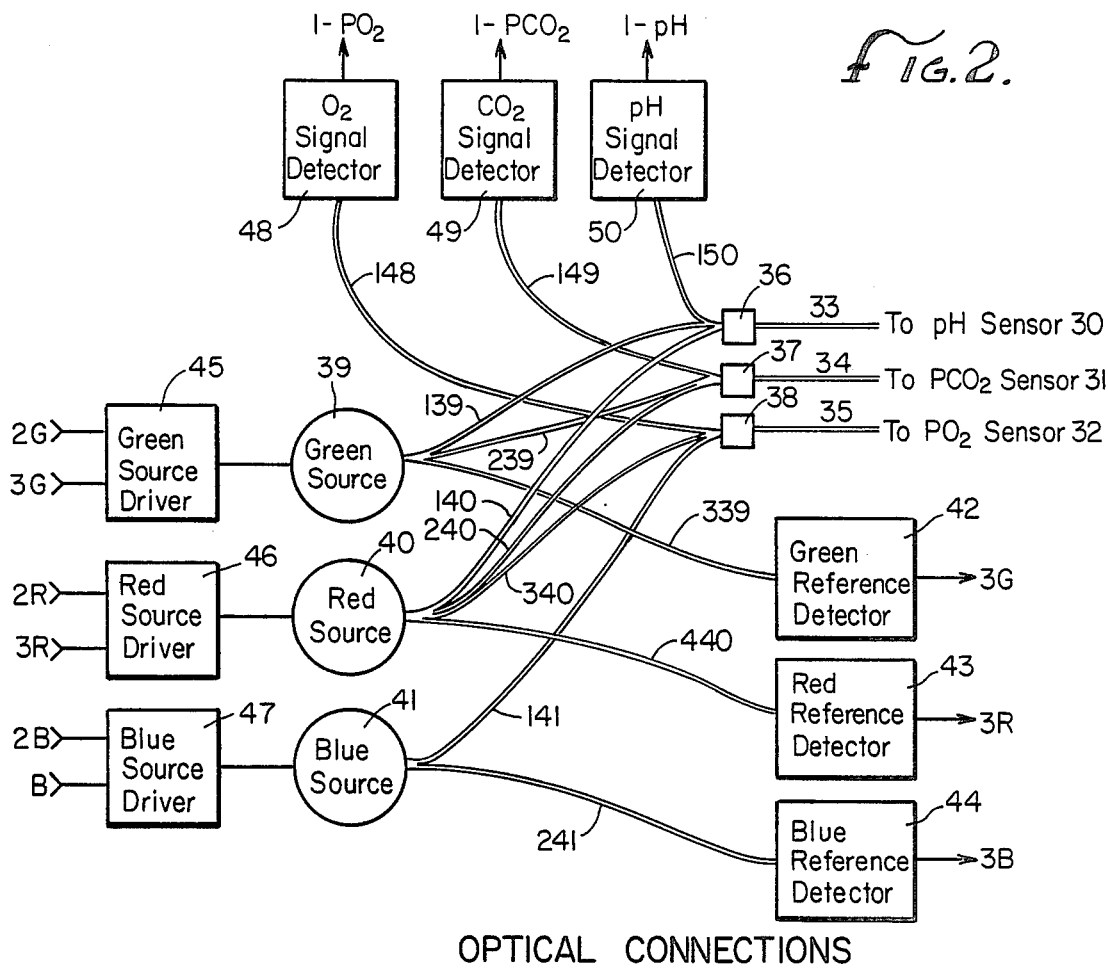
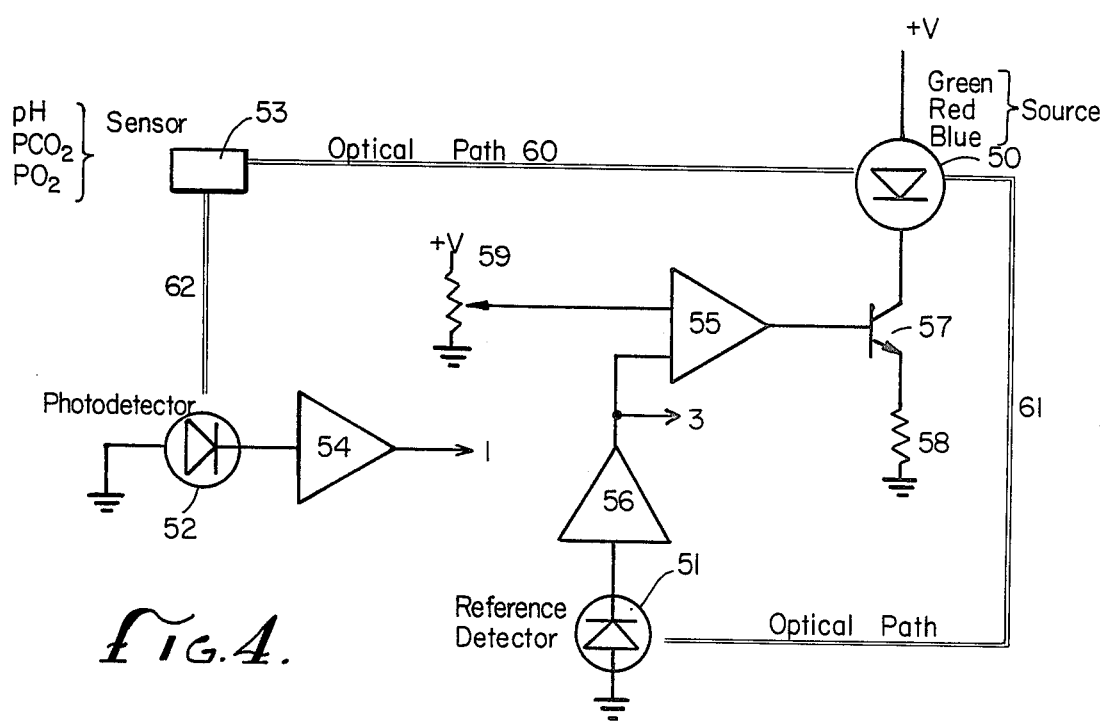

REFERENCE
DETECTION
CIRCUIT

DRIVER CIRCUIT

DRIVER CIRCUIT : BLUE LIGHT

DETECTION CIRCUIT

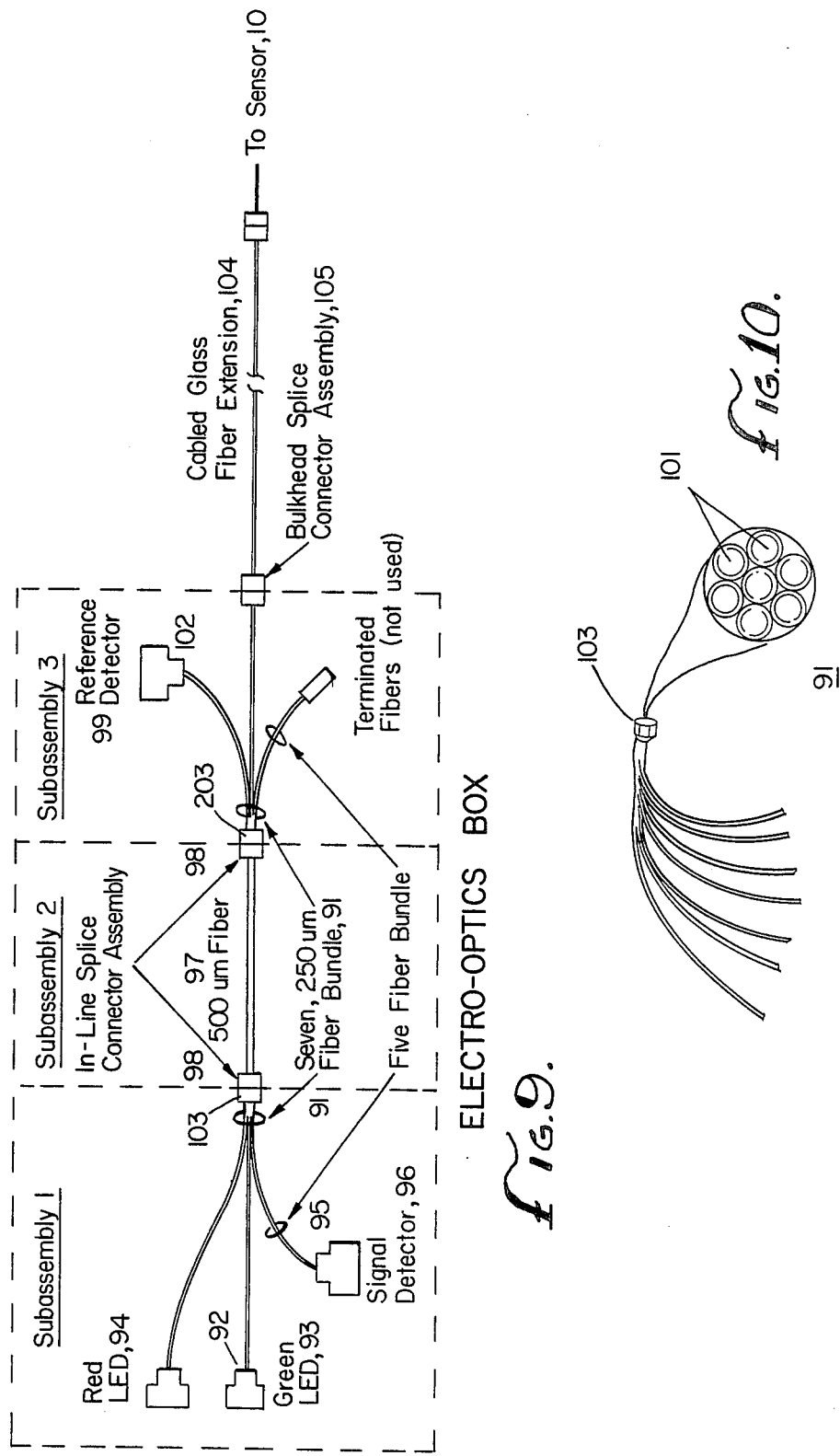

OPTOELECTRONICS SYSTEM FOR MEASURING ENVIRONMENTAL PROPERTIES HAVING PLURAL FEEDBACK DETECTORS

BACKGROUND OF THE INVENTION

This invention relates to an optoelectronics system and method for measuring one or more properties of an environment. In particular the invention relates to a system for measuring properties such as pH, $PCO_2$ and $PO_2$ of an environment by alternately transmitting light of two different wavelengths to the sensor and computing the value of the environmental property from the ratio of the two return light signals from the sensor. The invention is particularly useful for monitoring pH, $PCO_2$ and $PO_2$ in medical applications.

Various fiber optic chemical sensors have been developed recently, and particularly for use in medical applications. Fiber optic chemical sensors are based on the principle that the absorbance or fluorescence of a particular material changes with a particular property to be measured. For example, certain fiber optic pH sensors are based on the principle that the absorbance of the sensing material changes with pH of the surrounding environment. It has been found that a colorimetric pH indicating dye, such as phenol red, when bound to a polyacrylamide hydrogel by copolymerization of the dye with the acrylamide monomer produces a pH sensing material. The dye in the sensing material changes color with changes in pH and the color change corresponds to a change in the amount of light of a specified wavelength absorbed by the dye (e.g. green light in the case of phenol red). A fiber optic pH sensing probe consists of a pH sensing material bound to one or more optical waveguides. Light at a particular wavelength is transmitted down a waveguide to the pH sensor where the sensing material attenuates the light with respect to a second wavelength. This attenuated light is reflected or transmitted back down the same or another optical waveguide to a detector.

By changing the sensing element at the tip of the fiber optic probe, different properties of the environment can be measured. For example, phenol red bound to a polyacrylamide hydrogel can be used as a pH sensing medium; the addition of a bicarbonate solution to the pH sensing material produces a $PCO_2$ sensor, and the choice of an oxygen sensing medium such as a fluorescent dye chosen from the group of pyrene derivatives and perylene derivatives produces a $PO_2$ sensing sensor.

A pH sensing fiber optic probe is described in U.S. Pat. No. 4,200,110 to Peterson et al. Another fiber optic pH sensor is described in co-owned, co-pending application Ser. No. 747,488 filed June 21, 1985 titled "Fiber Optic pH Sensor Having Low Drift Rate", which is incorporated herein by reference. A fiber optic CO sensor is described in co-owned, co-pending application Ser. No. 877,572 filed June 23, 1986 titled "Fiber Optic $CO_2$ Sensor", which is incorporated herein by reference. Fiber optic sensors for measuring the partial pressure of oxygen are described in co-owned, co-pending application Ser. No. 698,282 filed Feb. 4, 1985 titled "Single Optical Fiber For Measuring the Partial Pressure of Oxygen" and Ser. No. 699,515 filed Feb. 7, 1985 titled "Optical Sensor for Monitoring the Partial Pressure of Oxygen", both of which are incorporated herein by reference.

Although fiber optic systems have been devised using light of a single wavelength, to achieve greater accuracy in measuring the particular chemical property of an environment, two different wavelengths of light are transmitted to the sensing material and the ratio of return light signals is computed. U.S. Pat. No. 3,799,672 to Vurek describes a device for monitoring blood oxygen saturation in which infrared radiation and visible red light are alternately shined through blood as it flows through a plastic cuvet. The ratio of the infrared signal to the red signal received by a phototransistor is computed by an electrical feedback system, the ratio being linearly related to blood oxygen saturation. Vurek uses two separate light sources to provide the two different wavelengths. Vurek recognized that the use of two separate light sources could introduce unreliability into the system due to drift, thermal changes and component aging. To eliminate some of these problems Vurek chose similar light sources for both light signals. In this case Vurek chose infrared and red LEDs. Vurek recognized that an advantage could be achieved when the signal for the denominator term in the ratio is maintained at a high level so that a good signal-to-noise ratio is maintained even at low saturation levels. To achieve this condition Vurek introduces a control or feedback system which alternately energizes the light sources such that the output of the second light source is controlled by and proportional to the optical signal of the first light source.

A major disadvantage of this scheme is that Vurek relies heavily on the fact that the LED output light power is directly and linearly related to input current. Vurek's system does not compensate for light sources whose output light is not directly and linearly related to input current, nor to light sources whose output light power or wavelength may change over time due to thermal effects and component aging.

U.S. Pat. No. 4,476,870 to Peterson describes a fiber optic oxygen sensing probe and system for measuring oxygen partial pressure in blood or tissue. Like Vurek, Peterson measures the ratio of the intensities of light of two different wavelengths to determine oxygen partial pressure. To minimize some of the problems associated with changes in light output from two light sources, Peterson uses a single light source which transmits light alternately through a blue filter and a green filter. In this way Peterson compensates for variations in light that are linearly related since they will be cancelled out in the ratio. However, Peterson's system does not compensate for changes in spectral output of the light source over time due to drift, temperature instability, etc., which are non-linear.

Therefore it is an object of the present invention to provide an optoelectronic system and method to measure chemical properties of an environment which is stable with respect to time, component aging and temperature variations.

It is another object of the present invention to provide an optoelectronic system and method which will measure the pH, $PCO_2$ and $PO_2$ of an environment.

Additional objects, advantages, and novel features of the invention will be set forth in part in the description which follows and in part will become apparent to those skilled in the art upon examination of the following or may be learned by practice of the invention.

SUMMARY OF THE INVENTION

To achieve the foregoing and other objects and in accordance with the principles of the present invention, a system for measuring at least one property of an environment may comprise a first light source for generating light at a first wavelength; first feedback means coupled to the first light source for maintaining the light from the first light source at a substantially constant level; a second light source for generating light at a second wavelength; second feedback means coupled to the second light source for maintaining the light from the second light source at a substantially constant level; a sensor to be placed in an environment, the sensor generating first and second optical output signals representing a change in the light from the first and second light sources, respectively, due to a property of the environment; means for transmitting light from the first and second light sources to the sensor; a detector for detecting the first and second optical output signals; means for transmitting the first and second optical output signals from the sensor to the detector; and computation means coupled to the detector for determining the value of the property of the environment from the first and second optical output signals. In particular, each feedback means may comprise a reference detector for detecting the light from the light source, the reference detector generating a reference signal in response to light from the light source; a comparator coupled to the reference detector for comparing the reference signal with a first reference value, the comparator generating an error signal in response to the difference between the reference signal and the reference value; and control means coupled to the light source for controlling the light generated by the light source in response to the error signal. By maintaining the light output from each light source substantially constant, variations due to time, component aging and temperature are overcome.

DESCRIPTION OF THE DRAWINGS

The present invention is illustrated in the accompanying drawings wherein:

FIG. 2 is a schematic diagram of a system for measuring pH, $PCO_2$ and $PO_2$.

FIG. 4 is a schematic representation of an optical feedback system according to the present invention.

FIG. 9 shows details of the optical connections for two light sources, a single sensor, and a reference detector.

FIG. 10 shows an expanded view of a seven fiber bundle which can be used in the present invention.

DETAILED DESCRIPTION OF THE PREFERRED EMBODIMENT

Figure 1:
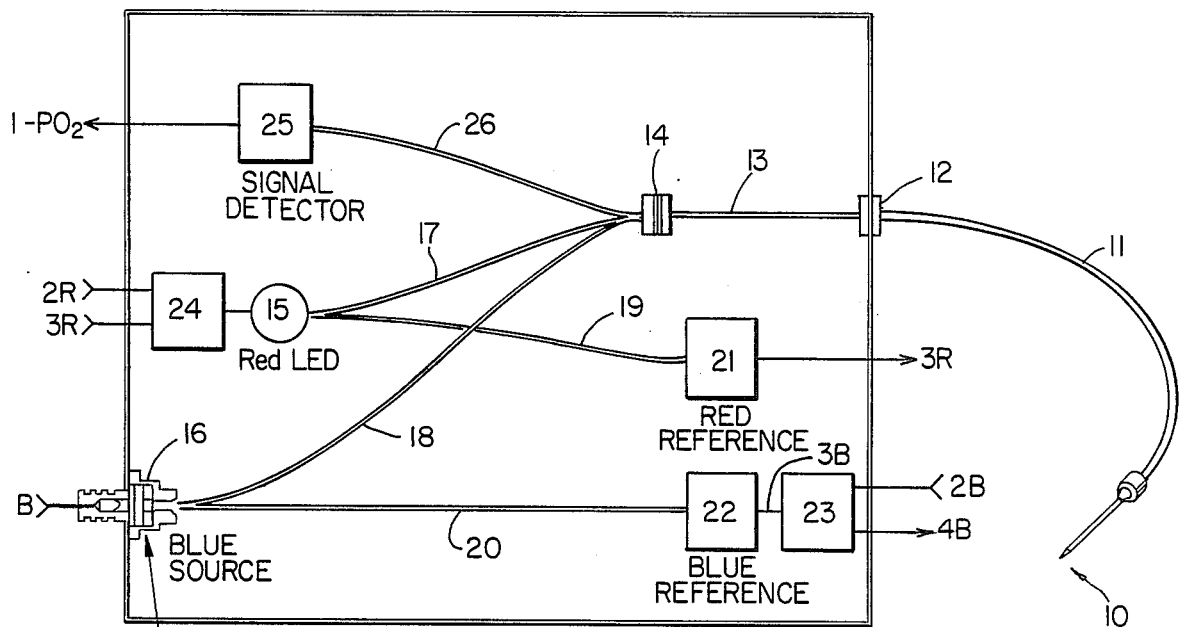
FIG. 1 is a schematic diagram of a system for measuring $PO_2$.

Referring to FIG. 1, a schematic of a system according to the present invention which measures a single property of an environment, in this case the partial pressure of oxygen, is shown. Chemical sensor 10, which is responsive to the partial pressure of oxygen, receives and transmits optical signals via fiber optic waveguide 11. Waveguide 11 is connected to waveguide 13 via connector 12. Since the chemical sensor is responsive to the partial pressure of oxygen the two different light sources are preferably chosen to be red and blue. Here, light from red LED 15 is transmitted via optical waveguide 17 to splice connector 14 and blue light from source 16 is transmitted to splice connector 14 via waveguide 18. Splice connector 14 combines the light from 17 and 18 into single fiber 13 which is transmitted via connector 12 to waveguide 11 to sensor 10. Return light signals from sensor 10 are transmitted back down waveguide 11 through connector 12 through waveguide 13 and splice connector 14 via waveguide 26 to detector 25. Detector 25 converts the optical signals from sensor 10 which represent a change in the light from the red and blue light sources due to the partial pressure of oxygen in the environment into electrical signals 1-$PO_2$ which are transmitted to the electronic control circuitry shown on FIG. 3.

In order to maintain the light power output of the red source 15 and blue source 16 at a substantially constant level, reference detectors are used in combination with a feedback circuit. Red source 15 transmits red light via optical waveguide 19 to red reference detector 21 and blue source 16 transmits blue light via optical waveguide 20 to blue reference detector 22. The red reference detector generates a red reference signal 3R which is combined with a control signal 2R from microprocessor 130 of the control circuit shown in FIG. 3 in red driver circuit 24. Similarly, blue reference detector 22 generates a blue reference signal 3B which is combined in blue driver circuit 23 with a control signal 2B from FIG. 3.

Figure 3:
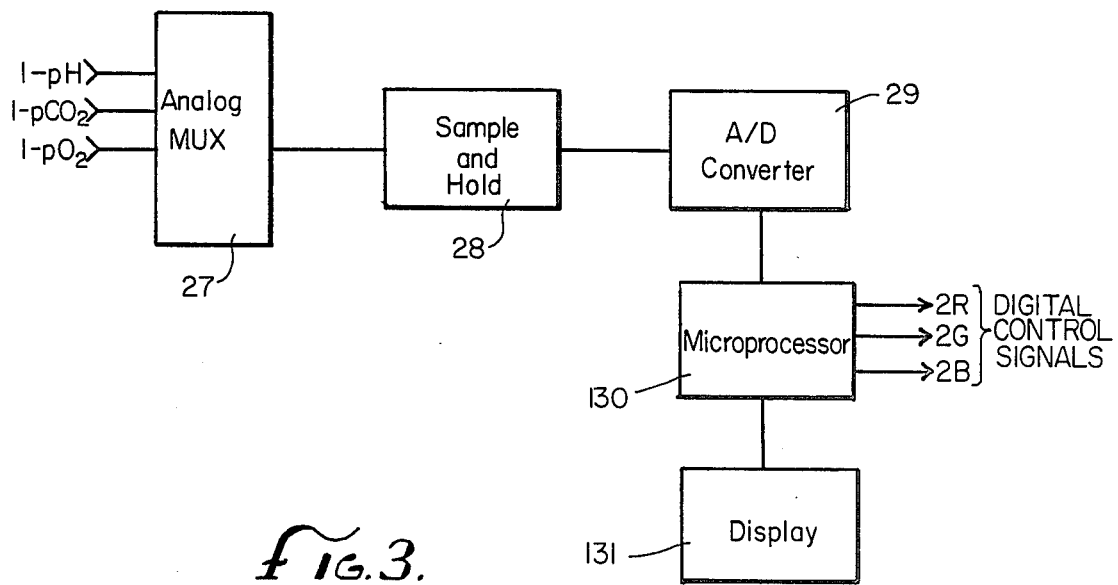
FIG. 3 is a schematic representation of a control system for the optical electronic system of FIGS. 1 and 2.

Referring to FIG. 3, the analog output signal, 1-$PO_2$, from the detector 25 is input into analog multiplexer 27. The analog multiplexer feeds the analog signals into sample and hold 28 which interfaces the analog signals to analog-to-digital converter 29. A/D converter 29 converts the analog output signals to digital signals which are fed to microprocessor 130 which then processes the signals and sends the results to the display 131. Microprocessor 130 also generates the digital control signals 2R and 2B which control the sequence of the red and blue sources via their respective drivers.

FIG. 2 shows the optoelectronic connections for a system according to the present invention in which three chemical properties are measured. In this embodiment three individual sensors which detect pH, $PCO_2$ and $PO_2$ are provided. Green and red light are preferably chosen for the two different wavelengths for both the pH sensor and the $PCO_2$ sensor and red and blue are preferably chosen as the two different wavelengths for the $PO_2$ sensor. Green light source 39 transmits green light via optical waveguide 139 to splice connector 36 to optical waveguide 33 to pH sensor 30. Similarly, green source 39 transmits green light via optical waveguide 239 via splice connector 37 via optical waveguide 34 to $PCO_2$ sensor 31. Green source 39 also transmits green light to green reference detector 42 via optical waveguide 339. Red light source 40 transmits red light to each sensor: via optical waveguide 140 to splice connector 36 to optical waveguide 33 to pH sensor 30; via optical waveguide 240 via splice connector 37 via waveguide 34 to $PCO_2$ sensor 31; via optical waveguide 340 via splice connector 38 via waveguide 35 to $PO_2$ sensor 32. Red source 40 also transmits red light to red reference detector 43 via optical waveguide 440. Blue source 41 transmits blue light via optical waveguide 141 through splice connector 38 to optical waveguide 35 to PO$_2$ sensor 32. Blue source 41 also transmits blue light to blue reference detector 44 via optical waveguide 241.

In this particular embodiment light from two sources is shown being combined in a splice connector, for example 36, into a single optical waveguide, for example 33, which is then transmitted to the sensor, for example 30. And a single fiber waveguide, 33, transmits the output signals from the sensor, 30, to the splice connector, 36, where it is transmitted to a detector, 50, via an optical waveguide, 150. It should be noted that while the invention has been described with respect to single fiber optical waveguides that the invention could be readily adapted to using a separate waveguide for transmitting the light from each source to the sensor and a separate waveguide for transmitting the optical output signals from the sensor to the detector.

Referring again to FIG. 2, PCO$_2$ sensor 31 generates optical output signals which are transmitted via waveguide 34 to splice connector 37 via optical waveguide 149 to PCO$_2$ detector 49. Similarly, PO$_2$ sensor 32 generates optical output signals which are transmitted via optical waveguide 35 via splice connector 38 via optical waveguide 148 to PO$_2$ detector 48. Each optical output signal from a particular sensor represents a change in the input light from a particular light source due to the value of the particular property of the environment to be measured.

Green reference detector 42 generates a reference signal 36 corresponding to the optical signal it receives from green source 39, this is fed to green source driver 45. Similarly, red reference detector 43 and blue reference detector 44 generate red and blue reference signals, 3R and 3B respectively, corresponding to the optical signals they receive from their respective light sources. These reference signals are fed, respectively, to red source driver 46 and blue source driver 47. Drivers 45, 46 and 47 also each receive control signals 2G, 2R, and 2B respectively, from microprocessor 130. Detectors 48, 49 and 50 generate electrical output signals 1-PO$_2$, 1-PCO$_2$ and 1-pH corresponding to the optical output signals received by their respective sensors. These signals are fed to analog multiplexer 27.

FIG. 4 shows a schematic representation of the optical feedback system according to the present invention. Light source 50 (which may be a green, red or blue source) generates light and transmits it via optical path 60 to sensor 53 (which may be a pH, PO$_2$ or PCO$_2$ sensor) and via optical path 61 to reference detector 51. Sensor 53 produces an optical output signal and sends it via optical path 62 to photodetector 52. Photodetector 52 generates an electrical signal which is amplified by amplifier 54. Reference detector 51 is also a photodetector and generates an electrical signal in response to the optical signal it receives from light source 50. This reference signal is amplified by amplifier 56 and is compared in error amplifier 55 with a predetermined output from potentiometer 59. Error amplifier 55 generates an error signal which is used to adjust the current driving the light source in order to maintain a constant optical output. The error signal, as shown in FIG. 4, is applied to the base of transistor 57 to determine the amount of current that drives light source 50 through load resistor 58. Alternatively, the output from error amplifier 55 could be used to adjust the voltage applied to a light source.

Figure 5:
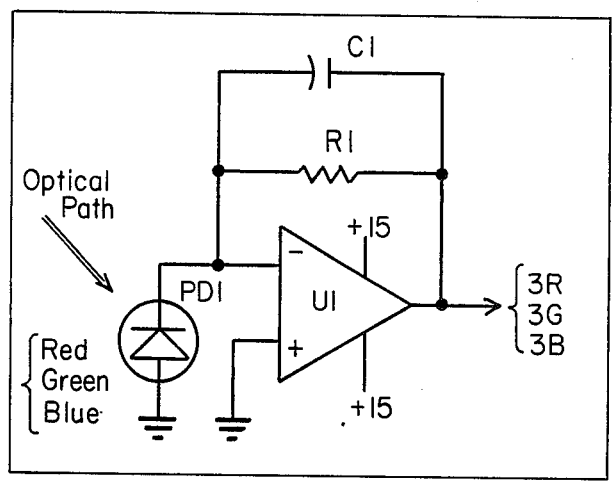
FIG. 5 shows further details of a reference detector circuit of FIGS. 1 and 2.

FIG. 5 shows a preferred embodiment for the reference detector circuit boxes 42, 43 and 44. In FIG. 5, photodetector PD1 generates current in response to light from an optical path which is fed into operational amplifier U1. The combination of capacitor C1, resistor R1 and op-amp U1 produces a current-to-voltage converter, which produces reference signal 3R, 3G, or 3B. Preferably, the operational amplifier is chosen to be model AD515 and the values of C1 and R1 are, respectively, 470 picofarads and 100 megohms.

Figure 6:
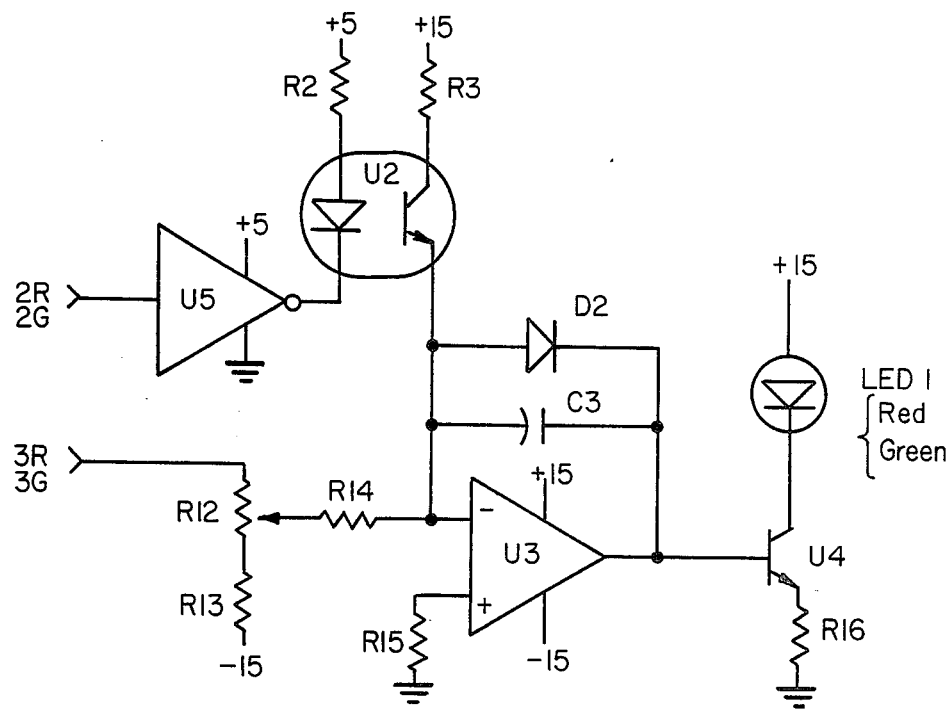
FIG. 6 shows a driver circuit for a LED source.

FIG. 6 shows preferred details of a driver circuit which can be used for drivers 45 and 46 for the red and green sources. This embodiment is preferable when the light source is controlled by current such as a light emitting diode. Reference signal 3R or 3G from the appropriate reference detector is subtracted from a reference value set by the potentiometer formed by resistors R12, R13 and R14. This output is integrated by operational amplifier U3 generating a control signal which determines the amount of voltage that is placed at the base of transistor U4. The amount of voltage on the base of transistor U4 determines the amount of current which drives LED1 through load resistor R16. When control signal 2R or 2G is at a digital high value, opto-isolator U2 is on, which applies +15 V through R3 to U3 forcing its output to a negative value limited by diode D2 which in turn shuts off U4. When control signal 2R or 2G is at a digital low value, optoisolator U2 is off, thus enabling the operational amplifier U3 to maintain the light output at LED 1 at a constant output determined by the setting of potentiometer R12, R13 and R14. Preferably digital gate U5 is model 7406, opto-isolator U2 is a 4N33, operational amplifier U3 is an AD642, transistor U4 is model 2N2222A. Preferably the value of resistor R2 is chosen to be 1,000 ohms, the value of R3 is chosen to be 10,000 ohms, the value of R12 is chosen to be 10,000 ohms, R13 is chosen to be 10,000 ohms, R14 is chosen to be 100,000 ohms, R15 is chosen to be 100,000 ohms, and R16 is chosen to be 200 ohms. Diode D2 is an IN4148 and capacitor C3 is chosen to be 0.47 microfarads.

Figure 7:
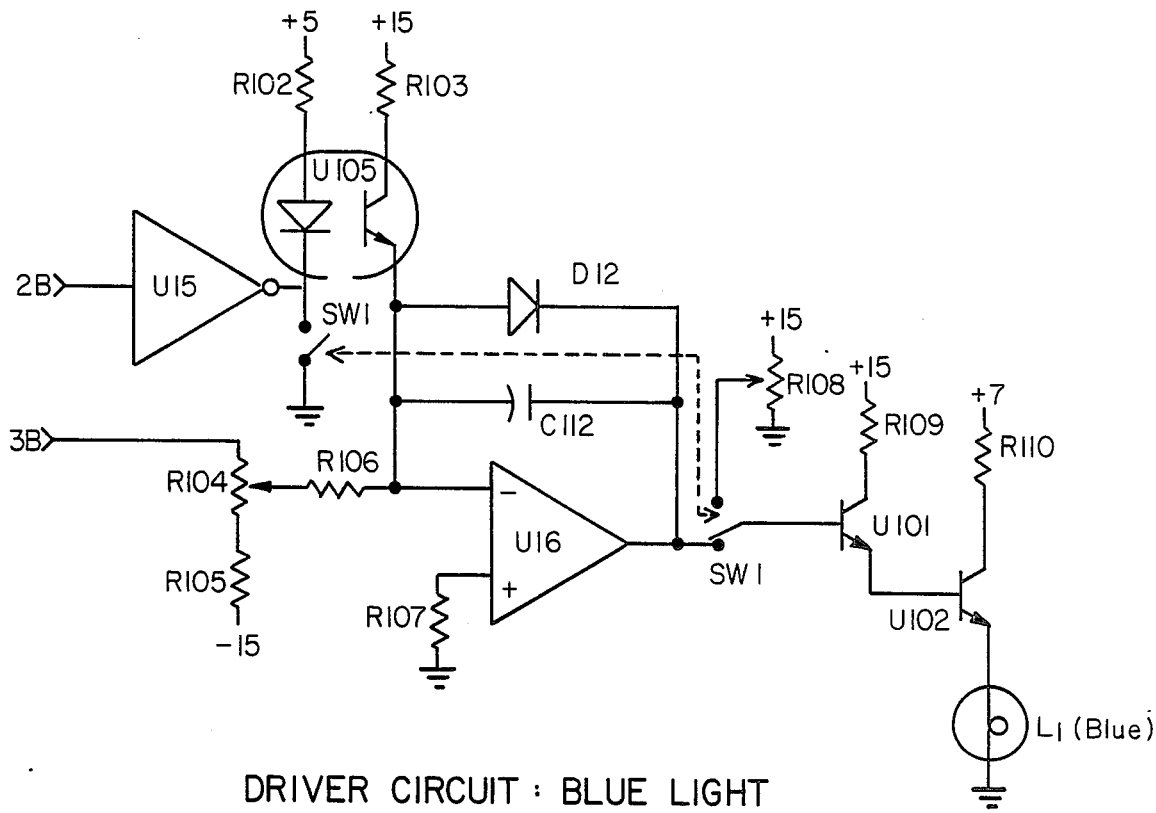
FIG. 7 shows a driver circuit for a blue incandescent light source.

FIG. 7 shows a driver circuit which may be used for a voltage driven light source. In this case, blue light is provided by a blue filtered incandescent light source L1. Referring to FIG. 7, reference signal 3B from the blue reference detector is subtracted from a reference value set in a potentiometer consisting of resistors R104, R105 and R106 and applied to operational amplifier U16, where it is integrated and generates a control signal. The control signal from operational amplifier U16 is applied to the base of the Darlington pair U101 and U102. The output of the Darlington pair, acting as an emitter-follower, sets the voltage across light source L1. The switch SW1 allows an optional constant voltage mode as opposed to a constant power mode, for use in diagnostics and instrument calibration. R108 sets the voltage in the constant voltage mode. In a manner similar to FIG. 6, control signal 2B enables and disables opto-isolator U105, which controls operational amplifier U16. Preferably, the values of resistor R104 is 10,000 ohms, R105 is 10,000 ohms, R106 is 100,000 ohms, R107 is 100,000 ohms, U15 is preferably a 7406, U105 is preferably a 4N33, the value of R102 is 1,000 ohms, R103 is 10,000 ohms, diode D12 is an IN4148, capacitor C112 is 1 microfarad, U16 is an AD642, R108 is 10,000 ohms, R109 is 470 ohms, U101 is a 2N2222A, U102 is a TIP29A and R110 is 4.7 ohms.

Figure 8:
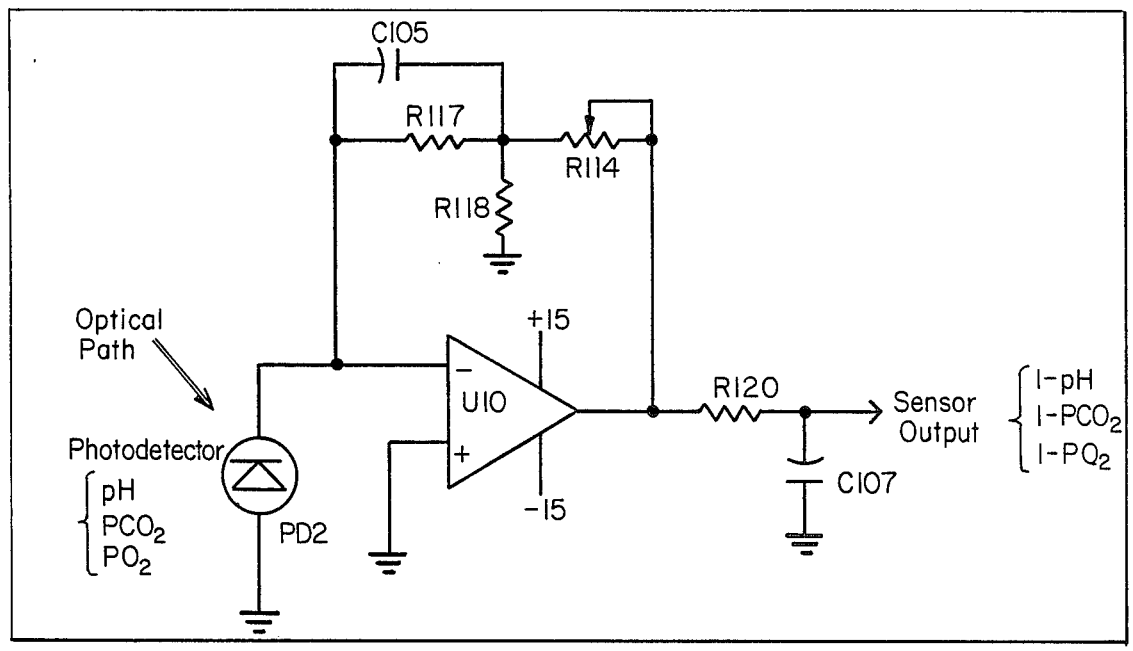
FIG. 8 shows a detection circuit.

FIG. 8 shows a preferred detection circuit which can be used for detector boxes 48, 49 and 50. Referring to FIG. 8, photodetector PD2 generates an electrical output signal in response to an optical signal. This is fed into a transimpedance amplifier which is formed by operational amplifier U10, capacitor C105, resistors R117, R114 and R118. The output of the transimpedance amplifier then is fed into a noise filter formed by R120 and capacitor C107 which produces electrical output signal 1-pH, 1-PCO$_2$ or 1-PO$_2$ which is then fed into the input of the analog multiplexer 27. Preferably amplifier U10 is an AD515, C105 is 100 picofarads, R117 is 1,000 megohms, R114 is 100,000 ohms, R118 is 1,000 ohms, R120 is 10,000 ohms and C107 is 4.7 microfarads.

DESCRIPTION OF AN EMBODIMENT OF THE OPTICAL SYSTEM

The modular, bidirectional optical fiber system designed for use with the fiber optic sensors has several functions. First, it combines the light emitted by two different light sources into a single optical fiber for delivery to the sensor. Second, it routes the light returning from the sensor to an optical detector for detection. Third, it provides a convenient means of monitoring the amount of light being delivered to the sensor from either light source.

As shown in FIG. 9, the optical fiber system for a pH sensor contains three subassemblies that are easily interconnected by means of commercially available optical fiber connectors. The first subassembly consists of a bundle 91 of seven, 250 $\mu$m O.D. plastic fibers 101 that is terminated with a 750 $\mu$m connector 103 at one end (see FIG. 10). At the opposite end of bundle 91 the central fiber is terminated with a 250 $\mu$m connector 92 and connected to a green LED 93. A second fiber is similarly terminated to a red LED 94. The remaining five fibers of the bundle are terminated with a 750 $\mu$m connector 95 and subsequently connected to an optical detector 96 for monitoring the amount of light returning from the sensor 10. The second subassembly consists of a single 500 $\mu$m O.D. plastic fiber 97 that is terminated at each end with a 530 $\mu$m connector 98. The third subassembly consists of a bundle 191 of seven, 250 $\mu$m O.D. plastic fibers 101 terminated at one end with a 750 $\mu$m connector 203. At the opposite end the central fiber of the bundle is terminated with a 250 $\mu$m connector 105. This fiber is in turn connected to a cabled glass extension fiber 104 and is used to deliver the optical power to the sensor as well as receive the return light. A second fiber of this bundle is also terminated with a 250 $\mu$m connector 102 and is mated to an optical detector 99 for monitoring the amount of light that is being delivered to the sensor (i.e., reference level). The remaining five fibers are not used at this time. The eight foot glass extension fiber 104 is also terminated at each end with a 250 $\mu$m connector.

METHOD OF OPERATION

Various computations can be programmed into microprocessor 130. Primarily, microprocessor 130 takes the value of the output signals from the detectors and computes the values of particular properties to be measured in the environment. In particular, the actual value of pH, PCO$_2$ and PO$_2$ may be determined. The system of the present invention can also include a calibration mode in which various physical constants of the system can be calculated as well as determining artifacts related to the optical system. In particular, microprocessor 130 can be programmed to calculate alpha which is the absorbance factor due to changes in path length of the optical system; K the protantation constant determined by the particular sensing material; and gamma the ratio of the two input light sources. In addition, the two artifact related values are dark level and backscatter level. Backscatter levels need only be determined when the particular sensors are attached to a single fiber for transmitting light to and from the sensor. Dark level is used to determine the detector offset values of the system.

To determine dark level for the system the sensors are placed in a neutral environment and the light sources are turned off, then the outputs from detectors 48, 49 and 50 are measured. Microprocessor 130 is then programmed to subtract the measured dark values from all future values. The backscatter of the optoelectronic system is determined by connecting a dummy sensor, i.e., a sensor with no sensing medium attached to it, to connector 12 of FIG. 1. The system is then operated by turning on light from red source 15 and blue source 16, in this example, and return light is measured at detector 25. The light level determined or measured at detector 25 is then stored in microprocessor 130. This backscatter light level is subtracted from all future system measurements.

The value of the pH of the particular environment may be calculated according to the following relationship:

$$pHi = LOGK - LOG\left[\frac{ALPHA}{QI + GAMMA} - 1\right], \quad (1)$$

WHERE $$Qi = -LOG\left[\frac{IGi - D - BG}{IRi - D - BR}\right],$$

WHERE
BG = GREEN BACKSCATTER,
BR = RED BACKSCATTER,
IGi = GREEN OUTPUT SIGNAL,
IRi = RED OUTPUT SIGNAL, and
D = DARK SIGNAL VALUE.

Note that both the dark signal value and the green and red backscatter values have been calculated prior to an individual measurement and these values have been stored in microprocessor 130 for use in equation (1). In addition for pH measurements the following calibration constants should be determined and the values stored in microprocessor 130 for implementation in the above equation. These calibration constants are LOGK, ALPHA and GAMMA. LOGK, ALPHA and GAMMA are calculated by taking three measurements for three known solutions and substituting them into the following relationships.

$$GAMMA = \frac{Q1*Q2*(B12-1) + Q2*Q3*(B23-1)*B12 - Q1*Q3*(B12*B23-1)}{Q3*(B12-1) + Q1*(B23-1)*B12 - Q2*(B12*B23-1)},$$

$$ALPHA = \frac{(Q1+GAMMA)*(Q2+GAMMA)*(B12-1)}{(Q2+GAMMA)*B12 - (Q1+GAMMA)}$$

$$LOG\,K = pH2 + LOG\left[\frac{ALPHA}{Q2 + GAMMA} - 1\right]$$

$$Bij = 10\,(pHi - pHj)$$

The value of the partial pressure of carbon dioxide is calculates according to the following relationship:

$$PCO_2 = K * \left[\frac{ALPHA}{Qi + GAMMA} - 1\right], \quad (2)$$

WHERE $$Qi = -LOG\frac{IGi - D - BG}{Iri - D - BR}$$

WHERE
- BG=GREEN BACKSCATTER,
- BR=RED BACKSCATTER,
- IGi=GREEN OUTPUT SIGNAL
- IRi=RED OUTPUT SIGNAL, and
- D=DARK SIGNAL VALUE.

Similarly, calibration constants K, ALPHA and GAMMA are also determined for the PCO$_2$ measurement in the same manner as for the pH measurement. ALPHA, GAMMA and K are determined from the following equations.

$$GAMMA = \frac{\frac{Q2*C2}{Q3-Q2} - \frac{Q3*C3}{Q3-Q2} + \frac{Q2*C2}{Q2-Q1} - \frac{Q1*C1}{Q1-Q1}}{\frac{C1}{Q2-Q1} - \frac{C2}{Q2-Q1} + \frac{C3}{Q3-Q2} - \frac{C2}{Q3-Q2}}$$

$$K = \frac{(Q2 + GAMMA)*C2 - (Q3 + GAMMA)*C3}{Q3 - Q2}$$

$$ALPHA = (Q2 + GAMMA) * (C2/K + 1)$$

The partial pressure of oxygen is calculated the following relationship.

$$PO_2 = A*Xi*Xi + B*Xi + C, \quad (3)$$

WHERE $$Xi = \left[\frac{IBi - DB - BB}{IRi - DR - BR}\right]$$

WHERE
- BB=BLUE BACKSCATTER,
- BR=RED BACKSCATTER,
- IBi=BLUE OUTPUT SIGNAL,
- IRi=RED OUTPUT SIGNAL,
- DB=BLUE DARK SIGNAL, and
- DR=RED DARK SIGNAL Calibration constants for partial pressure of oxygen are denoted by A, B, C and are calculated in the same manner as for pH, i.e., by measuring the output of three known solutions and calculating A, B, C according to the following relationships.

$$A = \frac{(P1 - P3)*(X1 - X2) - (P1 - P2)*(X1 - X3)}{(X1*X1 - X3*X3)(X1 - X2) - (X1*X1 - X2*X2)*(X1 - X3)}$$

$$B = \frac{(P1 - P2) - A*(X1*X1 - X2*X2)}{X1 - X2}$$

$$C = P1 - A*X1*X1 - B*X1$$

Microprossor 130 and display 131 can be combined into a commercially available system based on the model HP41CV calculator which uses the HP interface loop (HP-IL) for communication with an HP printer and HP cassette recorder and a multichannel analog to digital converter.

I claim:

1. A system for measuring at least one property of an environment comprising:
    a first light source for generating light at a first wavelength;
    first feedback means coupled to the first light source for maintaining the light from the first light source at a substantially constant level even as components age and thermal conditions vary;
    a second light source for generating light at a second wavelength;
    second feedback means coupled to the second light source for maintaining the light from the second light source at a substantially constant level even as components age and thermal conditions vary;
    a sensor to be placed in an environment, the sensor being responsive to a change in a property of the environment, the sensor generating first and second optical output signals representing a change in the light from the first and second light sources, respectively, due to a property of the environment;
    means for transmitting light from the first and second light sources to the sensor;
    a detector for detecting the first and second optical output signals;
    means for transmitting the first and second optical output signals from the sensor to the detector; and
    computation means coupled to the detector for determining the value of the property of the environment from the first and second optical output signals.

2. The system of claim 1 wherein the first feedback means comprises:
    a first reference detector for detecting the light from the first light source, the first reference detector generating a first reference signal in response to the light from the first light source;
    a first comparator coupled to the first reference detector for comparing the first reference signal with a first reference value, the first comparator generating a first error signal in response to the difference between the first reference signal and the first reference value; and
    first control means coupled to the first light source and to the first comparator for controlling the light generated by said first light source in response to said first error signal; and
    wherein said second feedback means comprises:
    a second reference detector for detecting the light from the second light source, the second reference detector generating a second reference signal in response to the light from the second light source;
    a second comparator coupled to the second reference detector for comparing the second reference signal with a second reference value, the second comparator generating a second error signal in response to the difference between the second reference signal and the second reference value; and second control means coupled to said second light source and to the second comparator for controlling the light generated by the second light source in response to the second error signal.

3. The system of claim 1 further comprising:

a plurality of sensors to be placed in an environment, each of the sensors being responsive to a change in a particular property of the environment, each of the sensors generating first and second optical output signals representing a change in the light from the first and second light sources, respectively, due to a property of the environment;

a plurality of means, one each for transmitting light from the first and second light sources to each of the sensors;

a plurality of detectors, one each for detecting the first and second optical output signals from each of the sensors; and a plurality of means, one each for transmitting the first and second optical output signals from each of said sensors to its corresponding detector.

4. A system for measuring pH, $PCO_2$ and $PO_2$ of an environment comprising:

a first light source for generating light at a first wavelength;

first feedback means coupled to the first light source for maintaining the light from the first light source at a substantially constant level even as components age and thermal conditions vary;

a second light source for generating light at a second wavelength;

second feedback means coupled to the second light source for maintaining the light from the second light source at a substantially constant level even as components age and thermal conditions vary;

a third light source for generating light at a third wavelength;

third feedback means coupled to the third light source for maintaining the light from the third light source at substantially constant level even as components age and thermal conditions vary;

a pH sensitive sensor to be placed in an environment, the pH sensor generating first and second optical output signals representing a change in the light from the first and second sources, respectively, due to the pH of the environment;

first means for transmitting light from the first and second light sources to the pH sensor;

a first detector for detecting the first and second optical output signals;

second means for transmitting the first and second optical output signals from the pH sensor to the first detector;

a $PCO_2$ sensitive sensor to be placed in an environment, the $PCO_2$ sensor generating third and fourth optical output signals representing a change in the light from the first and second light sources, respectively, due to the $PCO_2$ of the environment;

third means for transmitting light from the first and second light sources to the $PCO_2$ sensor;

a second detector for detecting the third and fourth optical output signals;

fourth means for transmitting the third and fourth optical output signals from the $PCO_2$ sensor to the second detector;

a $PO_2$ sensitive sensor to be placed in an environment, the $PO_2$ sensor generating fifth and sixth optical output signals representing a change in the light from the second and third light sources, respectively, due to the $PO_2$ of the environment;

fifth means for transmitting light from the second and third light sources to the $PO_2$ sensor;

a third detector for detecting the fifth and sixth optical output signals;

sixth means for transmitting the fifth and sixth optical output signals from the $PO_2$ sensor to the third detector; and computation means coupled to the detectors for determining the values of the pH, $PCO_2$ and $PO_2$ of the environment from the first and second optical output signals, the third and fourth optical output signals, and the fifth and sixth optical output signals, respectively.

5. The system of claim 4 wherein said first light source produces green light, said second light source produces red light, and said third light source produces blue light.

6. A method for measuring at least one property of an environment comprising the steps of:

(a) generating light at a first wavelength;

(b) maintaining the light at a first wavelength at a substantially constant level even as components age and thermal conditions vary;

(c) generating light at a second wavelength;

(d) maintaining the light at the second wavelength at a substantially constant level even as components age and thermal conditions vary;

(e) generating first and second optical output signals representing a change in the light at the first and second wavelengths, respectively, due to a property of the environment;

(f) detecting the first and second optical output signals; and (g) computing the value of the property of the environment from the first and second optical output signals.

7. The method of claim 6 wherein step (b) comprises the substeps of:

(b1) generating a first reference signal corresponding to light at the first wavelength;

(b2) comparing the first reference signal with a first reference value and generating a first error signal in response to the difference between the first reference signal and the first reference value; and (b3) controlling the light at the first wavelength in response to the first error signal.

8. The method of claim 7 wherein step (d) comprises the following substeps of:

(d1) generating a second reference signal representing the light at the second wavelength;

(d2) comparing the second reference signal with a second reference value and generating a second error signal in response to the difference between the second reference signal and the second reference value; and (d3) controlling the light generated at the second wavelength in response to the second error signal.

9. The system of claim 2, wherein said first control means adjusts the voltage applied to said first light source in response to said first error signal.

10. The system of claim 2, wherein said second control means adjusts the voltage applied to said second light source in response to said second error signal.

11. A system for measuring at least one property of an environment comprising:
- a first light source for generating light at a first wavelength;
- first feedback means coupled to the first light source for maintaining the light from the first light source at a substantially constant level even as components age and thermal conditions vary;
- a second light source for generating light at a second wavelength;
- second feedback means coupled to the second light source for maintaining the light from the second light source at a substantially constant level even as components age and thermal conditions vary;
- a sensor to be placed in an environment, the sensor being responsive to a change in a property of the environment, the sensor generating first and second optical output signals representing a change in the light from the first and second light sources, respectively, due to a property of the environment;
- means for transmitting light from the first and second light sources to the sensor;
- a detector for detecting the first and second optical output signals;
- means for transmitting the first and second optical output signals from the sensor to the detector; and
- computation means coupled to the detector for determining the value of the property of the environment from the first and second optical output signals;
- wherein said first feedback means comprises:
- a first reference detector for detecting the light from the first light source and producing a first reference signal in response to the light from said first light source;
- a first comparator coupled to the first reference detector for comparing the first reference signal with a first reference value, the first comparator generating a first error signal in response to the difference between the first reference signal and the first reference value; and
- a first current controlling means operatively connected to said first light source and to said first comparator for controlling the light generated by said first light source in response to said first error signal; and
- wherein said second feedback means comprises:
- a second reference detector for detecting the light from the second light source and producing a second reference signal in response to the light from said second light source;
- a second comparator coupled to the second reference detector for comparing the second reference signal with a second reference value, the second comparator generating a second error signal in response to the difference between the second reference signal and the second reference value; and
- a second current controlling means operatively connected to said second light source and to said second comparator for controlling the light generated by said second light source in response to said second error signal.

12. The system of claim 11, wherein said first current controlling means is a first transistor with its base operatively connected to said first comparator to receive said first error signal.

13. The system of claim 11, wherein said second current controlling means is a second transistor with its base operatively connected to said second comparator to receive said second error signal.

14. A system for measuring pH, $PCO_2$ and $PO_2$ of an environment comprising:
- a first light source for generating light at a first wavelength;
- first feedback means coupled to the first light source for maintaining the light from the first light source at a substantially constant level even as components age and thermal conditions vary;
- a second light source for generating light at a second wavelength;
- second feedback means coupled to the second light source for maintaining the light from the second light source at a substantially constant level even as components age and thermal conditions vary;
- a third light source for generating light at a third wavelength;
- third feedback means coupled to the third light source for maintaining the light from the third light source at a substantially constant level even as components age and thermal conditions vary;
- a pH sensitive sensor to be placed in an environment, the pH sensor generating first and second optical output signals representing a change in the light from the first and second sources, respectively, due to the pH of the environment;
- first means for transmitting light from the first and second light sources to the pH sensor;
- a first detector for detecting the first and second optical output signals;
- second means for transmitting the first and second optical output signals from the pH sensor to the first detector;
- a $PCO_2$ sensitive sensor to be placed in an environment, the $PCO_2$ sensor generating third and fourth optical output signals representing a change in the light from the first and second light sources, respectively, due to the $PCO_2$ of the environment;
- third means for transmitting light from the first and second light sources to the $PCO_2$ sensor;
- a second detector for detecting the third and fourth optical output signals;
- fourth means for transmitting the third and fourth optical output signals form the $PCO_2$ sensor to the second detector;
- a $PO_2$ sensitive sensor to be placed in an environment, the $PO_2$ sensor generating fifth and sixth optical output signals representing a change in the light from the second and third light sources, respectively, due to the $PO_2$ of the environment;
- fifth means for transmitting light from the second and third light sources to the $PO_2$ sensor;
- a third detector for detecting the fifth and sixth optical output signals;
- sixth means for transmitting the fifth and sixth optical output signals from the $PO_2$ sensor to the third detector; and
- computation means coupled to the detectors for determining the values of the pH, $PCO_2$ and $PO_2$ of the environment from the first and second optical output signals, the third and fourth optical output signals, and the fifth and sixth optical output signals, respectively;
- wherein said first feedback means comprises:
- a first reference detector for detecting the light from the first light source and producing a first reference signal in response thereto;

a first comparator coupled to the first reference detector for comparing the first reference signal with a first reference value, the first comparator generating a first error signal in response to the difference between the first reference signal and the first reference value; and a first control means operatively connected to said first light source and to said first comparator for controlling the light generated by said first light source in response to said first error signal;

wherein said second feedback means comprises:

a second reference detector for detecting the light from the second light source and producing a second reference signal in response thereto;

a second comparator coupled to the second reference detector for comparing the second reference signal with a second reference value, the second comparator generating a second error signal in response to the difference between the second reference signal and the second reference value; and a second control means operatively connected to said second light source and to said second comparator for controlling the light generated by said second light source in response to said second error signal; and wherein said third feedback means comprises:

a third reference detector for detecting the light from the third light source and producing a third reference signal in response thereto;

a third comparator coupled to the third reference detector for comparing the third reference signal with a third reference value, the third comparator generating a third error signal in response to the difference between the third reference signal and the third reference value; and a third control means operatively connected to said third light source and to said third comparator for controlling the light generated by said third light source in response to said third error signal.

* * * * *